United States Patent
Dimitriu

[19]
[11] Patent Number: 5,957,931
[45] Date of Patent: Sep. 28, 1999

[54] OBSTETRICAL VACUUM EXTRACTOR CUP

[75] Inventor: Dan G. Dimitriu, San Antonio, Tex.

[73] Assignee: Prism Enterprises, Inc., San Antonio, Tex.

[21] Appl. No.: 09/076,293

[22] Filed: May 11, 1998

[51] Int. Cl.⁶ .................................................. A61B 17/42
[52] U.S. Cl. ............................ 606/123; 606/124; 604/74
[58] Field of Search ................................... 606/123, 124; 604/74

[56] References Cited

U.S. PATENT DOCUMENTS

| | | | |
|---|---|---|---|
| D. 320,855 | 10/1991 | Smith et al. | D24/133 |
| 667,447 | 2/1901 | Miller . | |
| 674,738 | 5/1901 | Mills . | |
| 897,289 | 9/1908 | Howell . | |
| 1,782,814 | 11/1930 | Froehlich . | |
| 2,194,989 | 3/1940 | Torpin | 128/161 |
| 2,227,673 | 1/1941 | Price | 128/352 |
| 2,542,505 | 2/1951 | Gascoigne | 128/281 |
| 2,702,038 | 2/1955 | Uddenberg et al. | 128/161 |
| 3,202,152 | 8/1965 | Wood et al. | 128/361 |
| 3,263,683 | 8/1966 | Uddenberg | 128/303 |
| 3,592,198 | 7/1971 | Evans | 128/352 |
| 3,642,006 | 2/1972 | Wobbe | 128/361 |
| 3,765,408 | 10/1973 | Kawai | 128/352 |
| 3,794,044 | 2/1974 | Vennard et al. | 128/352 |
| 3,848,606 | 11/1974 | Chertkoff | 128/352 |
| 3,988,793 | 11/1976 | Abitbol | 5/365 |
| 4,014,344 | 3/1977 | Gutierrez | 128/361 |
| 4,127,632 | 11/1978 | Anger | 264/94 |
| 4,375,948 | 3/1983 | von Holdt | 425/437 |
| 4,512,347 | 4/1985 | Uddenberg | 128/352 |
| 4,620,544 | 11/1986 | O'Neil | 128/352 |
| 4,633,865 | 1/1987 | Hengstberger et al. | 128/303 R |
| 4,730,617 | 3/1988 | King | 128/352 |
| 4,794,915 | 1/1989 | Larsson | 128/64 |
| 4,799,922 | 1/1989 | Beer et al. | 604/74 |
| 5,019,086 | 5/1991 | Neward | 606/123 |
| 5,163,944 | 11/1992 | Neward | 606/123 |
| 5,224,947 | 7/1993 | Cooper et al. | 606/123 |
| 5,281,229 | 1/1994 | Neward | 606/123 |
| 5,308,321 | 5/1994 | Castro | 604/74 |
| 5,395,379 | 3/1995 | Deutchman et al. | 606/123 |
| 5,507,752 | 4/1996 | Elliott | 606/123 |
| 5,569,265 | 10/1996 | Elliott | 606/123 |
| 5,810,840 | 9/1998 | Lindsay | 606/123 |

FOREIGN PATENT DOCUMENTS

| | | |
|---|---|---|
| 0083328 | 7/1983 | European Pat. Off. . |
| 0527431 | 2/1993 | European Pat. Off. . |
| 1087487 | 2/1955 | France . |
| 3535-055 | 10/1985 | Germany . |

OTHER PUBLICATIONS

O'Grady et al., "Vacuum Extraction in Modern Obstetric Practice," pp. 13–21 (The Parthenon Publishing Group, Inc., New York, NY 1995).

Vacca, "Handbook of Vacuum Extraction in Obstetric Practice," pp. 1–12 (Edward Arnold, London, 1992).

Primary Examiner—Michael Buiz
Assistant Examiner—Jonathan D. Goldberg
Attorney, Agent, or Firm—Leydig, Voit & Mayer, Ltd.

[57] ABSTRACT

An obstetrical vacuum extractor comprising a vacuum cup to which a disk assembly and attached traction cord are rotatably coupled. The cup has a protrusion extending from its base, and the disk assembly a bore for receiving the protrusion. The protrusion is then preferably ultrasonically welded to create a button to rotatably retain the disk assembly on the cup.

12 Claims, 3 Drawing Sheets

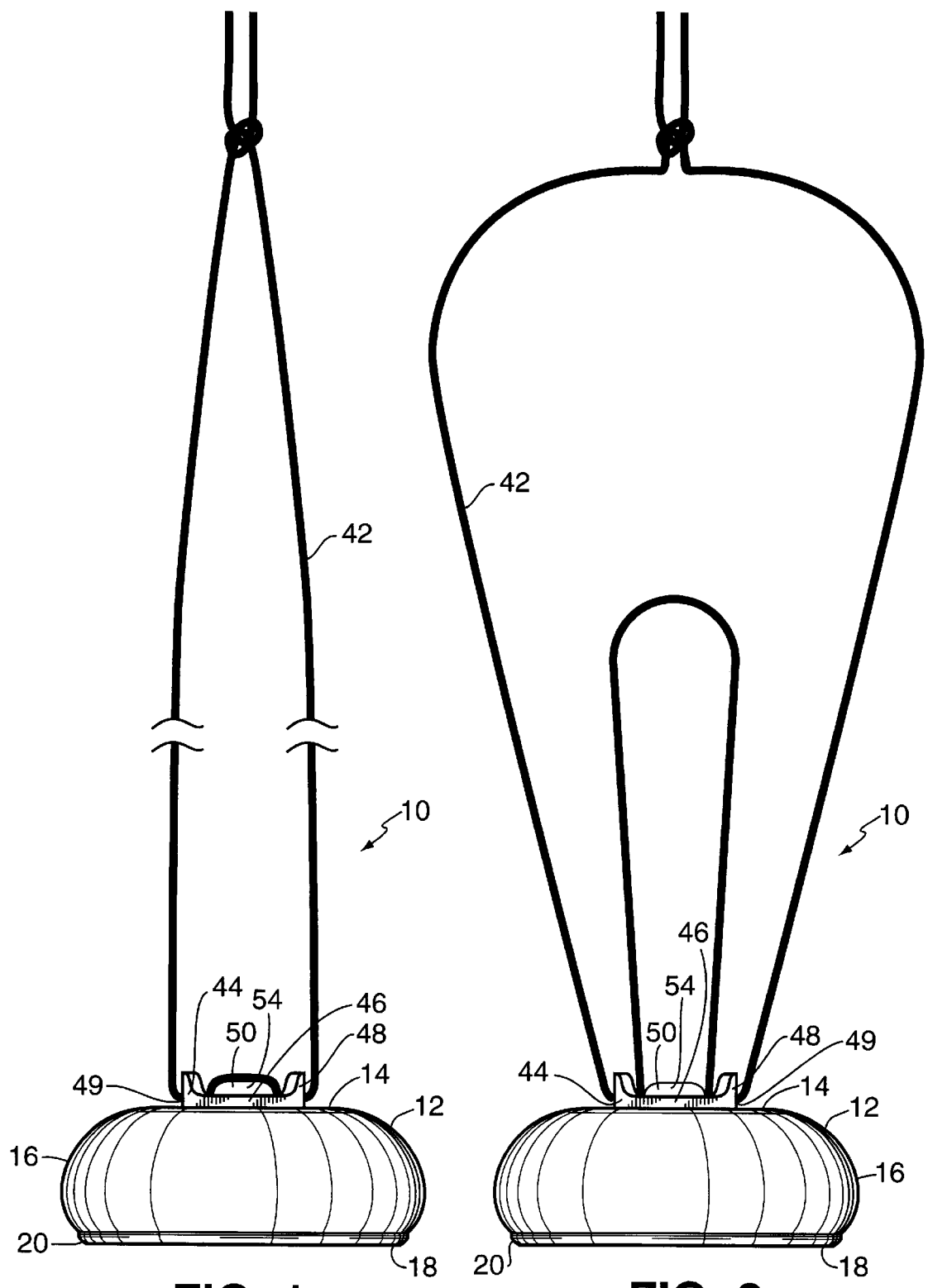

OBSTETRICAL VACUUM EXTRACTOR CUP

TECHNICAL FIELD OF THE INVENTION

The present invention relates to an apparatus for facilitating the delivery of a child during childbirth, and more specifically relates to vacuum extractors for use during childbirth.

BACKGROUND OF THE INVENTION

During childbirth, the birth mother is sometimes unable to deliver the child without assistance. In some cases, all that is required is for a nurse, midwife, or attending physician to push down on the birth mother's upper abdomen when she bears down during delivery. In other cases, it is necessary for a physician to perform a cesarean section. For those cases in between the two extremes, some sort of intermediate assistance is often required. Such intermediate assistance generally entails the use of some sort of device to aid in the delivery of the child. These devices may likewise be required to assist a physician during particularly difficult cesarean sections.

One example of such a device is forceps. Forceps, however, tend to be bulky and difficult to operate. In addition, the use of forceps, at the very least, is uncomfortable for the mother and infant and risks injury to both.

Alternative devices to forceps are obstetrical vacuum extractors. One example of such device is described in U.S. Pat. No. 5,019,086. The device comprises a cup, which may be placed onto the child's head, and an elongated hollow stem extending from the base or closed back wall of the cup. The elongated hollow stem is used to position the cup onto the infant's head and to introduce a vacuum pressure into the cup. This vacuum within the cup results in suction between the cup and the infant's head which is then used to maneuver and extract the infant from the birth canal by pulling in an appropriate direction on the gripping device coupled to the stem of the vacuum extractor. A similar device is manufactured and sold by Prism Enterprises, Inc. of San Antonio, Tex.

In the '086 patent, a portion of the stem/gripping device substantially adjacent the cup portion is provided with additional flexibility to permit the elongated stem to be folded into a position substantially parallel to the cup portion to facilitate insertion into the birth canal. While this device has been extremely effective and commercially successful, a device which facilitates a pulling force in plane parallel to the open end of the cup may be desirable when utilizing the device in occipitoposterior presentations, i.e., when the infant's head is disposed such that the crown extends toward the mother's tail bone.

Other examples of obstetric vacuum extractors which might more readily facilitate the exertion of a pulling force in a plane substantially parallel to the open end of the cup are disclosed in U.S. Pat. No. 5,803,926 to Neward (U.S. Ser. No. 08/488,492, which is awaiting issuance), U.S. Pat. No. 4,512,347 to Uddenberg, and U.S. Pat. No. 4,620,544 to O'Neil.

The Neward patent discloses a readily manufactured extractor device having a pair of arms with associated handles extending from opposite sidewalls of the cup. During insertion, one of the arms may be folded over the closed back surface of the cup to provide a low profile for insertion. One or both of the handles may then be used to maneuver the cup during delivery. While the relatively rigid arms of the cup may be used to maneuver the cup in a direction substantially parallel to the plane including the open edge of the cup, it may be difficult to exert a sufficient extraction pulling force in this same plane, but in a direction perpendicular to the direction in which the arms extend.

The Uddenberg reference presents a similar obstetric suction device which includes a two-point pulling arrangement in the form of a string, which extends around an arc of one-half of the cup, substantially adjacent the cup opening, the two ends of the string then extend from opposite sidewalls of the cup. The string is coupled to the cup by two loop-shaped attachments having laterally directed legs disposed within the rolled edge of the cup, and guiding loops disposed substantially adjacent the cup opening, just above the rolled edge. The two loop-shaped attachments are disposed at opposite positions on the sidewall. As with, the Neward device, the Uddenberg device can be difficult to exert a sufficient extraction force in every direction within the plane parallel to the closed back surface of the cup. Additionally, the Uddenberg cup can be expensive and time consuming to manufacture in that it requires both a number of separate components and multiple assembly operations.

The O'Neil cup is similarly quite expensive and time consuming to manufacture. The O'Neil cup is stainless steel and is formed with a recess with a peripherally inwardly facing flange around it. A separate circular metal plate is disposed within the recess below the flange, and a separate annular bearing is provided between the circular plate and the inwardly facing flange such that the circular plate is rotatable within the recess. A diametrically-directed arcuate rod is integrally formed with the circular plate. A ring to which a metal traction chain is attached is loosely held on the rod. While the O'Neil cup provides the user with additional degrees of movement in that the ring may slide back and forth on the rod, and the circular plate may rotate within the recess, the cup is very expensive to manufacture. Not only are the materials used in the cup expensive, but it includes multiple precision components which must be carefully assembled. The tolerances between the cup recess and the circular plate, as well as the annular bearing must be closely maintained in order to ensure proper operation of the cup.

OBJECTS OF THE INVENTION

It is a primary object of the present invention to provide a vacuum extractor which may be readily utilized in various infant presentations, but which may be economically and reliably manufactured. It is a related object to provide a vacuum extractor that may be manufactured using polymeric materials and conventional manufacturing techniques.

An additional object of the invention to provide a vacuum extractor cup that may be disposable without undue cost to the user.

More particular object of the invention is to provide a vacuum extractor cup that may be effectively utilized when the infant is presented in an occipitoposterior position. A further object of the invention is to provide a vacuum extractor cup that likewise may be readily utilized when the infant is in anterior or lateral presentations.

It is a more specific object of the invention to provide a vacuum extractor wherein an extraction force may be applied in substantially any direction within a plane parallel to the open edge of the cup, as well as any angle to the upper surface of the cup. A related object is to provide a vacuum extractor cup that will maintain sufficient extraction suction forces when a traction extraction force is applied to the cup.

These and other objects of the invention will become apparent upon review of the following description of the invention.

BRIEF SUMMARY OF THE INVENTION

The present invention provides an obstetrical vacuum extractor comprising a vacuum cup, which is preferably, substantially mushroom-shaped, and comprises a basal opening for placement against the head of the infant. A hollow stem, preferably extending from a sidewall of the cup, is adapted for connecting with a vacuum source which communicates with the inner cavity and basal opening of the cup. In order to facilitate maneuvering of the cup during delivery, a disk to which a traction cord is attached is rotatably coupled to the base or closed back portion of the cup, the closed back portion of the cup including a protrusion extending substantially perpendicular to the surface of the cup, and the disk including a mating bore for receiving the protrusion. The components are then preferably ultrasonically welded to flatten the protrusion into a button-like shape along the surface of the disk to rotatably couple the cup and disk. The string is threaded through two opening in arms extending upwardly from the surface of the disk.

Once the is properly placed on the infant's head, the disk may freely rotate relative to the cup as a traction force is applied to the string. Accordingly, the extraction force may be applied in substantially any direction relative to the cup. As a result, the cup may be effectively utilized in occipito-posterior presentations, as well as in anterior and lateral presentations.

The both the cup and disk of the invention are preferably formed of a polymeric material, and may be formed and assembled by conventional techniques, such as injection molding and ultrasonic welding, respectively. In this way, the assembly may be economically manufactured and assembled. Thus, a sanitized device may be used in a single application and then disposed of, without the effect being cost prohibitive to the user.

BRIEF DESCRIPTION OF THE DRAWINGS

FIG. 1 is a side view of an obstetrical vacuum extractor constructed in accordance with teachings of the present invention.

FIG. 2 is a side view of the obstetrical vacuum extractor of FIG. 1 wherein the traction cord is in an alternate position.

Figure 3:
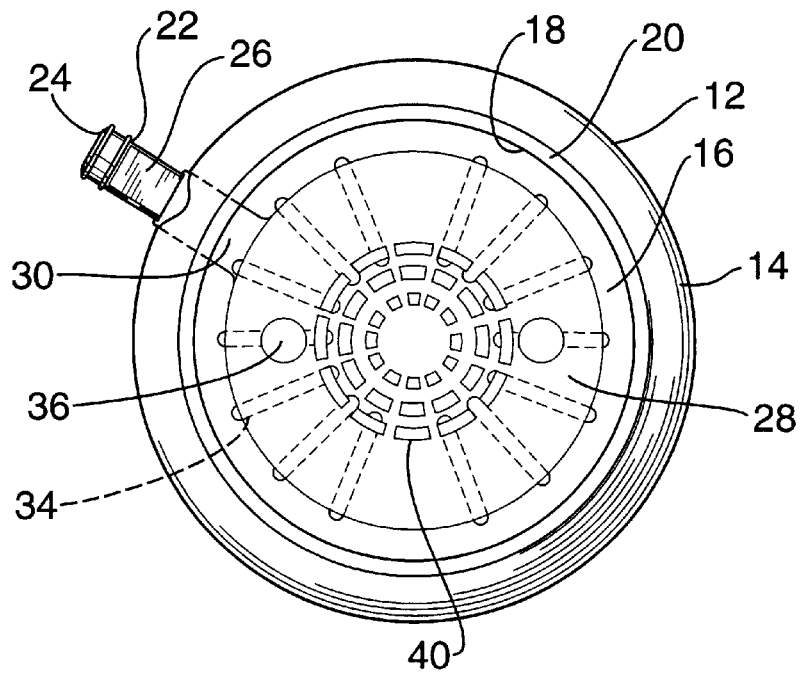
FIG. 3 is a bottom view of the obstetrical vacuum extractor of FIG. 1 without the traction cord attached.
Figure 4:
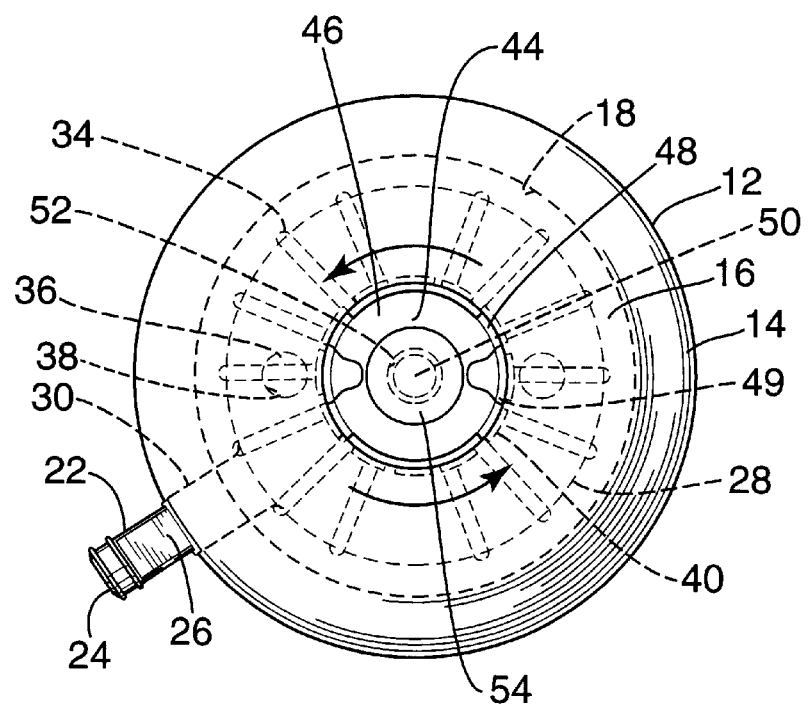
FIG. 4 is a top plan view of the obstetrical vacuum extractor of FIG. 1 without the traction cord attached.
Figure 5:
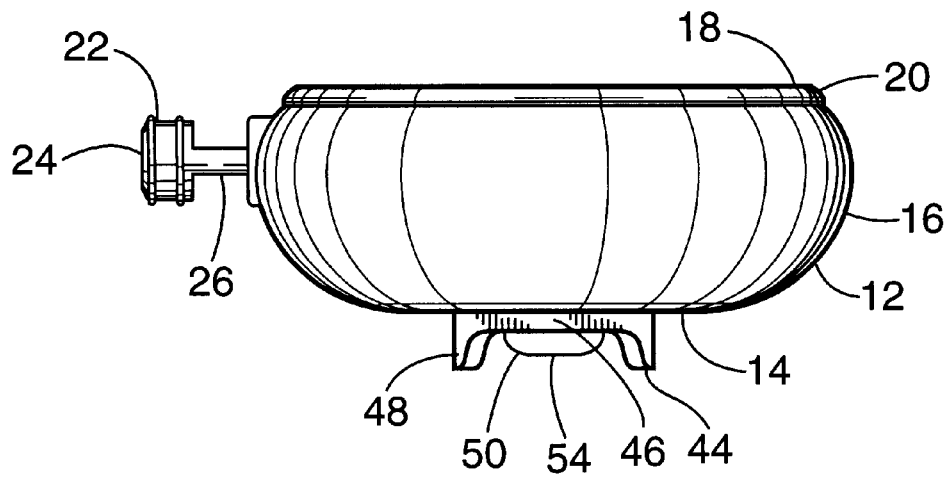
FIG. 5 is a side view of the obstetrical vacuum extractor of FIG. 1 without the traction cord attached.
Figure 6:
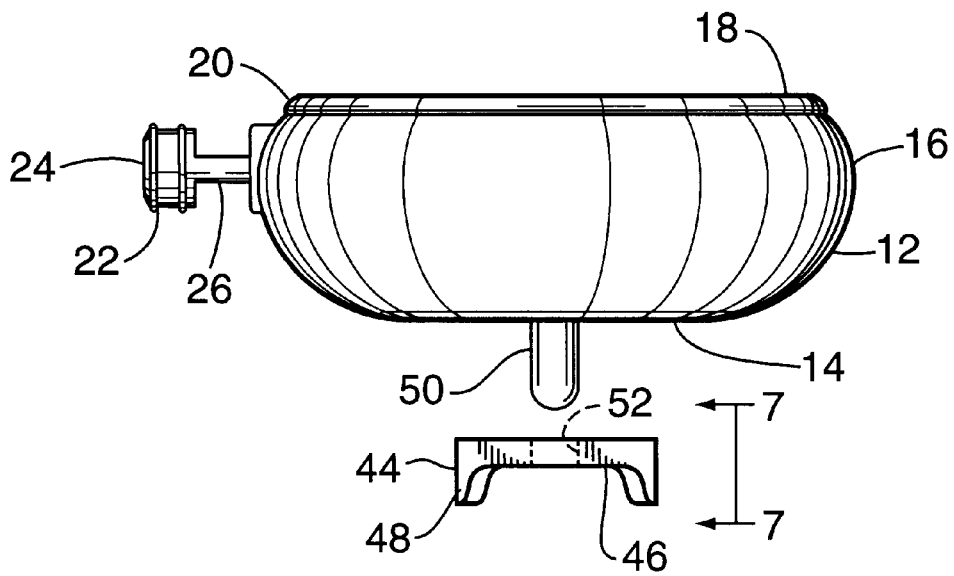
FIG. 6 is an exploded fragmentary side view of the obstetrical vacuum extractor similar to that shown in FIG. 5, prior to assembly of the disk to the cup.
Figure 7:
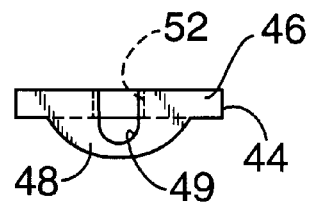
FIG. 7 is a side view of the disk assembly taken along line 7—7 in FIG. 6.

While the invention will be described in connection with preferred embodiments, there is no intent to limit it to those embodiments. On the contrary, the intent is to cover all alternatives, modifications, and equivalents included within the spirit and scope of the invention as defined by the appended claims.

DETAILED DESCRIPTION OF THE INVENTION

Turning now to the drawings, there is shown in FIG. 1 an obstetrical vacuum extractor 10 for use in assisted delivery techniques. The vacuum extractor 10 comprises a hollow vacuum cup 12 having a back wall or base 14 and an annular side wall 16 which opens into a basal opening 18 for placement against the head of a child. In the embodiment illustrated, the vacuum cup 12 is in the general shape of a mushroom or bowl, having a ridge 20 with a smooth or rounded contour around the basal opening 18 of the cup 12 to provide a gentle and effective contact with the scalp of the child. The overall dimensions of the vacuum cup 12 are such that the vacuum cup 12 may be easily inserted into the birth canal and properly positioned onto the child's head.

In order to achieve a vacuum or reduced pressure within the cup 12 during delivery, the cup 12 is provided with a hollow stem 22 (see FIGS. 3–6), a passageway 24 extending therethrough which opens into the inside of the cup 12. A flexible vacuum line from a suitable vacuum source can be attached to stem 22 to draw a vacuum or lower pressure within the cup 12 to secure the same to the head of an infant during delivery (not illustrated). The stem 22 may extend from the sidewall 16 of the cup 12 as shown, or from the base 14. To facilitate flexure of the stem 22 during placement and delivery, the stem 22 preferable includes a flattened section 26.

In order to distribute the vacuum force within the cup 12, a disk 28 having a tab 30 is provided within the interior of the cup 12, spaced from the inside surface of the base 14, as shown in FIG. 3. The tab 30 may be separate from or integrally formed with the disk 28. The tab 30 is disposed over, but spaced from the opening of the passageway 24 into the interior of the cup 12 by ribs extending inward from the sidewall 16 of the cup 12 and/or ribs extending from the tab 30 toward the sidewall (not shown), adjacent the opening of the passageway 24.

The disk 28 is likewise spaced from the inside surface of the base 14 by ribs 34 extending from the inside surface of the base 14. The disk 28 is preferably coupled to the cup 12 by protrusions 36 which extend from the inside wall of the base 14 and are assembled through bores 38 in the disk 28 and ultrasonically welded by conventional techniques. The disk 28 further includes a series of openings 40 for distributing the vacuum throughout the cup 12. It will be appreciated by those skilled in the art that the tab 30 prevents the skin of the baby's head from being drawn into the opening of the passageway 24, and, rather, directs the vacuum between the disk 38 and the inside surface of the base 12 so that it is distributed by the openings 40 and ribs 34.

To facilitate delivery, the obstetrical vacuum extractor 10 is provided with a traction cord 42. In accordance with the invention, the traction cord 42 is coupled to the cup 12 by disk assembly 44. (See FIGS. 1–2 and 4–6.) According to an important feature of the invention, the disk assembly 44 is rotatably coupled to the base 14 of the cup 12, such that it rotates as indicated by the arrows shown in FIG. 4. In this way, the traction cord 42 is free to rotate to whatever position is most advantageous during the delivery process as an extraction force is exerted on the traction cord 42.

The disk assembly 44 includes a base portion 46 and one or more upright arms 48 having bores 49 through which the traction cord 42 may be inserted. While the base portion 46 is relatively flat and of a circular, disk-like configuration in the embodiment illustrated, the base portion may be of a alternate configuration, so long as it does not present any harsh edges that might damage the maternal tissue. Preferably, the disk assembly 44 includes two upright arms 48, such that the traction cord 42 may be manipulated relative to the cup 12 to either the position shown in FIG. 1 or the position shown in FIG. 2, as preferred by the physician. In the embodiment illustrated, the arms 48 have an arched configuration. As with the base portion 46, however, they may be of an alternate configuration, so long as they do not present any harsh edges.

In order to rotatably couple the disk assembly 44 to the cup 12, the cup 12 is provided with a protrusion 50, and the base portion 46 of the disk assembly 44 is provided with a bore 52 for receiving the protrusion 50. As seen most clearly in the exploded view of FIG. 6, the protrusion 50 extends outward from the cup base 14 in a substantially perpendicular manner. The bore 52 is of a slightly larger diameter than the protrusion 50 such that when it is assembled onto the protrusion 50, the disk assembly 44 may rotate freely. Once the disk assembly 44 is placed onto the cup 12, the end of the protrusion 50 is widened, by ultrasonic welding, or the like, to develop a "button" 54 to secure the disk assembly 44 to the cup 12. It will be appreciated by those skilled in the art that the button 54 retains the disk assembly 44 on the cup 12, while, importantly, the disk assembly 44 remains free to rotate relative to the cup 12. Additionally, the extractor 10 maintains a low profile such that it may be readily utilized in occipitoposterior presentations where there is little maneuvering space.

Both the cup 12 and the disk assembly 44 are preferably formed of a polymeric material. Further, both components may be formed of conventional molding techniques, such as injection molding. As a result, the extractor 10 may be economically molded and assembled. In this way, the extractor 10 may constructed as a single use, disposable device, without prohibitory fabrication costs.

The loop formed by the traction cord 42 as shown in FIG. 1 is preferably on the order of 17½ inches in circumference. The traction cord 42 may be of a rope type configuration or a chain type configuration, and may be formed of any appropriate material, which may be sterilized by preferably conventional sterilizing techniques.

While the vacuum extractor 10 according to the current invention has been described in connection with a substantially mushroom shaped cup 12, it will be appreciated that the cup might be of an alternate design, and still provide benefits of the invention.

While this invention has been described with emphasis upon the preferred embodiment, it will be obvious to those of ordinary skill in the art that the preferred embodiment may be varied. Accordingly, this invention includes all modifications encompassed within the spirit and scope of the appended claims.

What is claimed is:

1. An obstetrical vacuum extractor for placement on a child's head for use during childbirth, the obstetrical vacuum extractor comprising, in combination, a vacuum cup having a cup base and a side wall defining a hollow interior cavity, the cup base having an exterior surface, the side wall having a side wall edge forming a cup opening, the vacuum cup further including a vacuum opening communicating with the interior cavity of the vacuum cup and being adapted for connection to a vacuum source, the vacuum cup further comprising a protrusion extending from the exterior surface of the cup base, the protrusion having an end;

a disk assembly rotatably coupled to the vacuum cup, the disk assembly having a disk base portion and at least one arm extending therefrom, the disk base portion having a bore extending therethrough for receiving the cup protrusion during assembly, the end of the protrusion being enlarged during assembly to rotatably couple the disk assembly to the cup; and a traction cord coupled to the arm for rotation with the disk assembly relative to the cup.

2. The obstetrical vacuum extractor of claim 1 wherein the arm includes an arm bore, the traction cord extending through the arm bore.

3. The obstetrical vacuum extractor of claim 1 wherein the disk assembly includes a pair of arms extending from the disk base portion, each arm including an arm bore, the traction cord extending through the arm bores.

4. The obstetrical vacuum extractor of claim 1 wherein the cup is molded of a polymeric material.

5. The obstetrical vacuum extractor of claim 1 wherein the disk assembly is molded of a polymeric material.

6. The obstetrical vacuum extractor of claim 5 wherein the vacuum cup is molded of a polymeric material.

7. The obstetrical vacuum extractor of claim 1 wherein the protrusion is ultrasonically welded to the disk assembly to create the button.

8. The obstetrical vacuum extractor of claim 4 wherein a protrusion is ultrasonically welded to the disk assembly to create the button.

9. The obstetrical vacuum extractor of claim 6 wherein the protrusion is ultrasonically welded to the disk assembly to create a button.

10. The obstetrical vacuum extractor of claim 1 wherein the disk base is a substantially annular.

11. The obstetrical vacuum extractor of claim 1 wherein a vacuum opening is disposed in the sidewall of the cup.

12. The obstetrical vacuum extractor of claim 11 wherein the vacuum opening is disposed in the cup base.

\* \* \* \* \*

UNITED STATES PATENT AND TRADEMARK OFFICE
CERTIFICATE OF CORRECTION

PATENT NO. : 5,957,931
DATED : September 28, 1999
INVENTOR(S) : Dan G. Dimitriu

It is certified that errors appear in the above-identified patent and that said Letters Patent is hereby corrected as shown below:

In Claim 7, column 6, line 36, "the button" should read "a button".

In Claim 8, column 6, line 39, "the button" should read "a button".

In Claim 10, column 6, line 44, "is a substantially annular" should read "is substantially annular".

Signed and Sealed this

Second Day of May, 2000

Q. TODD DICKINSON

Attest:

*Attesting Officer*          *Director of Patents and Trademarks*